United States Patent
Larsen et al.

(10) Patent No.: US 10,757,948 B2
(45) Date of Patent: Sep. 1, 2020

(54) PRE-STUNNING OR STUNNING OF ANIMALS WITH A COMBINATION OF $O_2$, $CO_2$ AND $NO_2$

(71) Applicant: Teknologisk Institut, Taastrup (DK)

(72) Inventors: Helle Daugaard Larsen, Taastrup (DK); Leif Lykke, Taastrup (DK); Margit Dall Aaslyng, Taastrup (DK); Lars Ole Blaabjerg, Taastrup (DK); Pia Brandt, Taastrup (DK)

(73) Assignee: Teknologisk Institut, Taastrup (DK)

( * ) Notice: Subject to any disclaimer, the term of this patent is extended or adjusted under 35 U.S.C. 154(b) by 357 days.

(21) Appl. No.: 15/578,986

(22) PCT Filed: Jun. 2, 2016

(86) PCT No.: PCT/EP2016/062490
§ 371 (c)(1),
(2) Date: Dec. 1, 2017

(87) PCT Pub. No.: WO2016/193368
PCT Pub. Date: Dec. 8, 2016

(65) Prior Publication Data
US 2018/0132495 A1    May 17, 2018

(30) Foreign Application Priority Data
Jun. 2, 2015 (DK) .................... 2015 00320

(51) Int. Cl.
*A22B 3/00* (2006.01)
*A61M 16/16* (2006.01)
(Continued)

(52) U.S. Cl.
CPC .............. *A22B 3/005* (2013.01); *A22B 1/00* (2013.01); *A22B 7/001* (2013.01); *A61M 16/12* (2013.01);
(Continued)

(58) Field of Classification Search
CPC .................... A22B 3/00; A22B 3/005
(Continued)

(56) References Cited

U.S. PATENT DOCUMENTS 5,487,699 A * 1/1996 Tyrrell .................... A22B 3/00
452/53
5,788,564 A * 8/1998 Chamberlain ......... A22B 3/005
452/66
(Continued)

FOREIGN PATENT DOCUMENTS

DE    10 2012 100 480 B3    5/2013
DK         2617288 T3       7/2013
(Continued)

*Primary Examiner* — Richard T Price, Jr.
(74) *Attorney, Agent, or Firm* — Holland & Hart LLP

(57) ABSTRACT

When stunning animals e.g. by $CO_2$-stunning aversive reactions may be seen among the animals as a reaction to the high concentration of $CO_2$. To avoid the aversive reactions animals can be pre-stunned before being final-stunned and perhaps killed or slaughtered when stunned. Pre-stunning of animals may be performed with a combination of gas for pre-stunning comprising at least air and/or $O_2$ together with $CO_2$ e.g. in a concentration below 40%, at least air and/or O2 together with N2O, or at least air and/or $O_2$ together with $N_2O$ and $CO_2$, where $CO_2$ may bi in a concentration below 40%. For larger animals such as pigs pre-stunning is performed for less than 60 seconds. A stunning system may comprise means for pre-stunning of animals before performing a final-stunning and may include gas storage for re-use of the pre-stunning gas.

15 Claims, 2 Drawing Sheets

(51) Int. Cl.
  *A61M 16/12* (2006.01)
  *A22B 1/00* (2006.01)
  *A22B 7/00* (2006.01)

(52) U.S. Cl.
  CPC ..... *A61M 16/16* (2013.01); *A61M 2202/0208* (2013.01); *A61M 2202/0225* (2013.01); *A61M 2202/0283* (2013.01); *A61M 2205/84* (2013.01); *A61M 2250/00* (2013.01)

(58) Field of Classification Search
  USPC .............................................. 452/52, 57, 66
  See application file for complete search history.

(56) References Cited

U.S. PATENT DOCUMENTS

| | | | |
|---|---|---|---|
| 7,448,943 B1* | 11/2008 | Woodford | A22B 3/005 452/66 |
| 2005/0191953 A1* | 9/2005 | Ovesen | A22B 3/00 452/66 |
| 2006/0172673 A1* | 8/2006 | Cattaruzzi | A22B 3/00 452/57 |
| 2006/0183414 A1* | 8/2006 | Zachariassen | A22B 3/00 452/66 |
| 2008/0051019 A1* | 2/2008 | Lang | A22B 3/005 452/66 |
| 2008/0254727 A1* | 10/2008 | Lang | A22B 3/005 452/66 |
| 2015/0040892 A1 | 2/2015 | Wilson, Jr. | |
| 2015/0250192 A1* | 9/2015 | Thulin | A22B 3/005 452/57 |

FOREIGN PATENT DOCUMENTS

| | | |
|---|---|---|
| EP | 1 495 678 A1 | 1/2005 |
| FR | 2 863 453 A1 | 6/2005 |
| JP | 2005 143389 | 6/2005 |

\* cited by examiner

PRE-STUNNING OR STUNNING OF ANIMALS WITH A COMBINATION OF $O_2$, $CO_2$ AND $NO_2$

The present invention relates to a gas combination and method for pre-stunning and optionally final stunning of animals with a combination of air and/or $O_2$, together with $CO_2$ and/or $N_2O$, such as air with $O_2$, together with $CO_2$ and $N_2O$. The method may be used before animals are final-stunned prior to their slaughter or for killing these animals. The method may also be as an integrated part of the stunning process.

BACKGROUND OF INVENTION

Stunning of animals such as pigs and chicken with high concentration of $CO_2$ is debated by scientists and in the media. There is a general consensus that the method of group-wise $CO_2$-stunning is the best method available up until the actual stunning. An aversive reaction may occur in the animals prior to stunning. The aversive reaction includes un-resting and/or panic-like behavior among the animals. The aversive reaction lasts 10-30 seconds, and this is the only part of the process that is subject to a quite rigorous debate. $CO_2$-stunning is close to ideal concerning handling of living animals, and concerning the quality of the stunning, and concerning meat quality such as reduced drip-loss and hemorrhages, when performed according to the recommendations. No other stunning methods perform nearly as well as $CO_2$-stunning. Most high capacity slaughter houses use $CO_2$-stunning.

At abattoirs pigs must be stunned in a quick stunning process e.g. by exposure to $CO_2$ where high concentration of $CO_2$ of above 60% secure a quick stunning process, however most of such pigs show aversive reactions.

The present invention relates to a method to avoid or relieve the aversive reaction to the high $CO_2$-concentrations, and with a correctly performed group wise $CO_2$-stunning a method including pre-stunning and final-stunning would be a close to perfect method concerning animal welfare and meat quality e.g. reduced drip loss and hemorrhages. The present invention may also be performed as an integrated part of the stunning process.

The pre-stunning step e.g. performed as an integrated part of the stunning process is also believed to contribute to the reduction of muscle hemorrhages in ham and tenderloins, that are considered a significant source of economic loss by the slaughterhouse industry.

DE102008003865 describes pre-stunning and final-stunning of pigs by guiding pigs into a chamber filled with inert gas such as argon for pre-stunning, and conveying the pigs further into another chamber filled with carbon-di-oxide for final-stunning and where the pigs hang with head down during the final-stunning. This pre-stunning of pigs is different than the present invention. It is undesirable to manage pigs during the stunning process such that operators suspend the pigs, as this includes burdensome working positions for the operators.

WO 98/31231 ('A procedure and equipment for treating poultry before slaughter') and WO 99/60861 ('A method and equipment for the production of a gas mixture') describe a procedure and equipment for the treatment, such as anaesthetisation or killing, of poultry by using gas. The gas comprises oxygen and carbon dioxide, among other components. The concentration of carbon dioxide is increased either continuously or discontinuously. In the equipment the poultry are exposed to the gas in a chamber, that may comprise a belt conveyer and further be separated into three treatment zones.

WO 94/15469 ('Method and device for stunning of poultry') describes a method and device for stunning of poultry, which poultry are taken into a first chamber to contain a first stunning gas or gas mixture, and the poultry are subsequently taken into a second chamber which is essentially separated from the first chamber as regards gas and which contains a second stunning gas or gas mixture for increasing the stunning achieved in the first chamber. The oxygen concentration may in the first chamber be at least 15% by vol. Preferably, the stunning gas in this case comprises carbon dioxide in a concentration of at least 25% by vol., but nitrous oxide, ether, cyclopropane or halothane can also be used as the stunning gas.

WO 01/91563 ('Method and apparatus for at least stunning an animal for slaughter') relates to a method for at least stunning an animal for slaughter, comprising two processing steps of: a) reducing the consciousness of the animal for slaughter using a gas, and b) administering to the animal for slaughter with reduced consciousness at least one electrical pulse in order to influence the heart function of the animal for slaughter. The invention also relates to an apparatus for at least stunning an animal for slaughter, comprising: a gas stunning space with means for gas feed, and electrical stunning means. The stunning gas comprises at least 30% $CO_2$.

None of the described prior-art methods use a combination of $CO_2$, $O_2$ and $N_2O$ for a pre-stunning or stunning process.

In the stunning method described herein which includes a pre-stunning step the animals are handled as little as possible by operators to avoid stressing the animals while they are conscious.

SUMMARY OF INVENTION

The invention relates to a combination of gas for pre-stunning and optionally final stunning of at least one animal, where the gas combination comprises
  at least air and/or $O_2$, together with $CO_2$ in a concentration below 40%,
  at least air and/or $O_2$, together with $N_2O$, or
  at least air and/or $O_2$, together with $N_2O$ and $CO_2$, where $CO_2$ is in a concentration below 40%.

Preferably the pre-stunning and optionally final stunning of at least one animal is performed with a gas mixture comprising $O_2$ (e.g. from air), $N_2O$ and $CO_2$.

The concentration of $CO_2$ may be below 60% such as below 40%.

This gas is a pre-stunning gas and the combination of gas may be such that the concentration of $O_2$ is between 1 and 26% and the concentration of $CO_2$ is between 1 and 40%, and/or the concentration of $N_2O$ is between 1 and 75%. Any remaining part of the gas combination may be air, preferably such that the concentration of $O_2$ is kept below about 26%.

It is believed that the presence of air or $O_2$ in the pre-stunning gas is important to avoid aversive reactions among the animals to be pre-stunned. Pre-stunned animals may be final-stunned to become stunned e.g. prior to slaughter of the at least one animal.

The combination of gas i.e. the pre-stunning gas can be used for pre-stunning of at least one animal. Pre-stunning may be performed for a very short time such as between 2 and 300 sec to avoid the aversive reactions when the at least one animal is exposed to a final-stunning gas for final-stunning.

Pre-stunning with a pre-stunning gas mentioned herein may be performed on any animal such as a livestock. Preferably the at least one animal is pigs, cattle, dairy cows, goats, deer, poultry, rabbits. The at least one animal may be pre-stunned one by one or group wise.

The invention also relates to a method for pre-stunning and optionally final stunning of at least one animal. The method may comprise the steps of:
- Directing the at least one animal into a system configured for pre-stunning with at least one gas which preferably is a pre-stunning gas,
- Introducing the combination of gas into the system, where the introducing of gas is performed with a mixed or a non-mixed gas combination preferably a pre-stunning gas,
- Keeping the at least one animal in the system with the combination of gas for at least 2 seconds, such as at least 5 seconds,
- Whereby the at least one animal is pre-stunned.

The method when performed with pigs, goats, sheep, deer, rabbits and poultry is preferably performed on at least two animals such that the pre-stunning is performed as a group-wise pre-stunning method. Large animals such as cattle and dairy cows may be pre-stunned individually or group-wise. At small abattoirs individually pre-stunning may be preferred for all animals to be slaughtered.

The method may further comprise a final-stunning step performed after pre-stunning of the at least one animal in the pre-stunning gas.

The method may further comprise a slaughtering step where the at least one pre-stunned and final-stunned animal is slaughtered. For sanitation the method may comprise a pre-stunning step and a final-stunning step where the final-stunning step is performed until the at least one animal is killed.

The invention further relates to a system for pre-stunning of at least one animal, where the system comprises
- At least one pre-stunning chamber comprising an entrance and an exit for entrance and exit of at least one animal, optionally the at least one animal can be enclosed in a gondola or a movable chamber such as a box,
- At least one gas inlet for directing at least $O_2$, $CO_2$ and $N_2O$ or a combination of these gasses e.g. in air into the pre-stunning chamber,
- At least one gas outlet for evacuating gas from the pre-stunning chamber,
- A control system adapted to control the operation of
  - directing gas into the pre-stunning chamber,
  - optionally controlling maintaining a pre-determined concentration of each of the gasses during the pre-stunning step and
  - evacuating gas from the pre-stunning chamber.

The gas inlet for $O_2$ may be a gas inlet for air.

The system may comprise at least one gas storage for storage of pre-stunning gas, such as for re-use of pre-stunning gas within the system.

The system may further comprise boxes or gondolas for transporting or conveying the at least one animal through a pre-stunning step and a final-stunning step. The final-stunning may be performed in a pit with a final-stunning gas such as at least 60% $CO_2$ when stunning of pigs or ruminants.

DETAILED DESCRIPTION OF THE INVENTION

Figure 1:
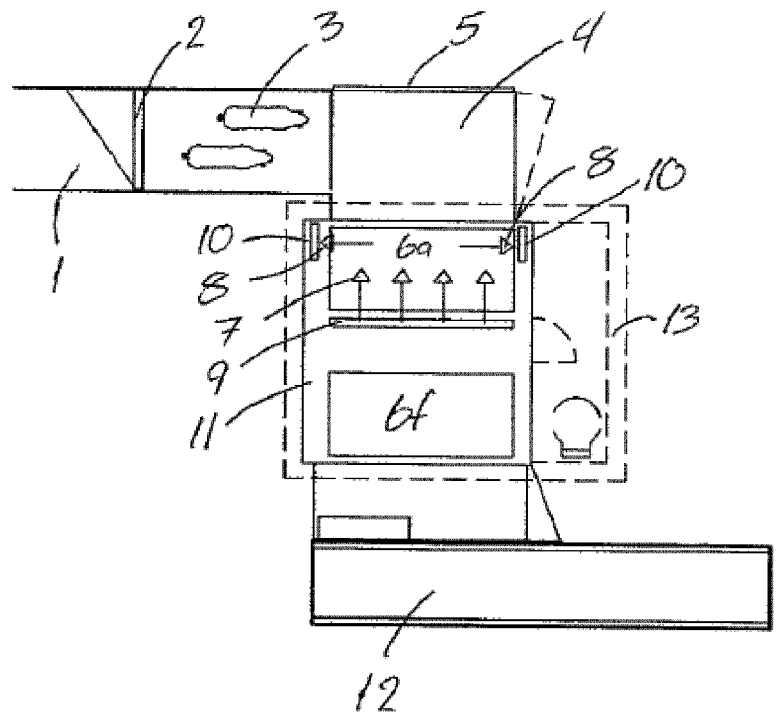
FIG. 1 illustrates a stunning system for pigs seen from above.

An aspect the present invention relates to a combination of gas for pre-stunning and optionally final stunning of at least one animal, the combination comprises
- at least air and/or $O_2$, together with $CO_2$ e.g. in a concentration below 40%,
- at least air and/or $O_2$, together with $N_2O$, or
- at least air and/or $O_2$, together with $N_2O$ and $CO_2$, where $CO_2$ is in a concentration below 60%, such as below 40%.

Preferably the pre-stunning and optionally final stunning of at least one animal is performed with a gas mixture comprising $O_2$ (e.g. from air), $N_2O$ and $CO_2$.

Preferably the concentration of $CO_2$ is below 60%, such as below 40%.

The gas used for pre-stunning is not metabolized by the animals to be stunned.

Pre-stunning may be
- a separate step performed before a step of stunning (=final stunning),
- may be performed as an integrated part of a stunning process i.e. in the first part of the stunning process, or
- may be performed as a separate step before the stunning process and also as an integrated part of the stunning process.

Pre-stunning is performed to obtain at least one pre-stunned animal. In this respect a pre-stunned animal is an animal which is relaxed, calm downed, sedated, unconscious and/or pain relieved. Pre-stunned animals may thus be conscious. Most animals which are pre-stunned would show and/or experience less or no aversion reaction when final-stunned with $CO_2$ in comparison to animals which are not pre-stunned before $CO_2$-stunned. Final stunning may be performed by gas stunning such as $CO_2$-stunning, stunning with a captive bolt device such as a bolt pistol or by electric stunning.

The invention therefore also relates to methods for stunning of at least one animal, where the method comprises the steps of:
1. Pre-stunning of at least one animal with a gas mixture as described herein,
2. Final-stunning of the at least one pre-stunned animal by
   - Gas stunning such as $CO_2$-stunning,
   - Captive bolt device stunning or
   - Electric stunning.

It is important to avoid lack of oxygen during the pre-stunning period i.e. oxygen must be present during the pre-stunning, in order to avoid the aversive effect and/or excitation following oxygen depletion that can be observed when inert gasses are used for stunning. $N_2O$ provides a light sedating or stunning effect, and an increase in $CO_2$ concentration compared to the $CO_2$-concentration in air increases the respiratory depth and frequency, and also an initiation of the stunning process. Sufficient oxygen secures that the sedation/pre-stunning is not due to a "strangling effect".

The combination of the analgetic and calming effect of $N_2O$, combined with increased respiration caused by a low $CO_2$-concentration may be able to eliminate or at least decrease the aversive reaction of pigs and other animals during the induction phase of a $CO_2$ stunning. $N_2O$ is furthermore very quickly eliminated from the animal body, making it suitable for consumption afterwards.

An animal's reaction to pre-stunning with a gas combination as described herein is individual and may be dependent on the animal's weight, age, respiration system and difference in pattern of reactions etc. Thus for animals with similar age and nearly same weight, which has been raised under similar conditions and which are pre-stunned together, different reactions may be observed as an effect of the pre-stunning where some of the animals may be conscious although relaxed and others may be unconscious. An effect of pre-stunning of animals is preferably taken as an average of a number of animals and may be determined from multiple tests to determine gas concentration and duration of the pre-stunning process to obtain a satisfactory result.

The desired effect on the animals can range from a light sedation to unconsciousness, depending on which is found to be working best under production conditions. The object of the pre-stunning of animals is to avoid the 10-30 seconds of aversive reaction to the high (>70%) $CO_2$-concentrations normally used in $CO_2$-stunners.

The desired effect of pre-stunning may also be determined depending on the stunning system used. A increased effect may be required if pre-stunning is performed as a separate step before final stunning, whereas a lower effect may be required if pre-stunning is performed as an integrated part of the stunning process. The increased effect in a system where the pre-stunning is performed as a separate step before final stunning should preferably secure the animals are kept at least sedated until the final stunning begins to have an effect on the animals, such that aversive reactions are avoided. The desired effect may be obtained by performing the pre-stunning for a longer or shorter time, where the duration of the pre-stunning may be as described elsewhere herein.

A preferred combination of gas for pre-stunning of at least one animal is at least air and/or $O_2$, together with $N_2O$ and $CO_2$, where $CO_2$ is in a concentration below 40%.

The pre-stunning gas as described herein may be a gas combination wherein
the concentration of $O_2$ is between 5 and 26% and
the concentration of $CO_2$ is between 1 and 40%, and/or
the concentration of $N_2O$ is between 5 and 75%.

In a preferred embodiment the remaining part of the gas is air.

The concentration of $O_2$ in the pre-stunning is preferably 10-21%. Oxygen may be present in the pre-stunning gas by the amount normally being present in atmospheric air and this concentration may be obtained by using atmospheric air as part of the pre-stunning gas. The gas combination may be produced by adding a predetermined amount of $CO_2$ and/or $N_2O$ into atmospheric air. The gas combination may also be produced by mixing $O_2$ with $CO_2$ and/or $N_2O$, or by mixing atmospheric air with $O_2$ and with $CO_2$ and/or $N_2O$. The mixing process may occur before the gas combination is directed towards the animals to be pre-stunned or the mixing process may be performed directly in the chamber where the animals are to be pre-stunned.

The $O_2$ concentration of the pre-stunning gas may also be 10-15%, 13-19% or 15-21%, such as about 15%.

The concentration of $CO_2$ in the pre-stunning gas is preferably 5-40%, such as 5-30%, e.g. 10-30%, such as 10-20%, e.g. 15-40%.

The concentration of $N_2O$ in the pre-stunning gas is preferably 5-75%, such as 50-75%, e.g. 35-60%, such as 35-55%, e.g. 30-50%, such as 40-50%, e.g. 10-65%, such as 15-50%, e.g. 20-40%, such as 10-30%, e.g. 5-25%. $N_2O$-concentration above 30% is preferred.

With gas concentration mentioned by '%' is meant volume % of the gas.

Preferably the pre-stunning gas does not include any inert gasses. Although if atmospheric air is used to produce the pre-stunning gas any inert gasses in the air is accepted in the pre-stunning gas.

Pre-stunning with $O_2$ (e.g. from air), $CO_2$ and/or $N_2O$ is used to optimize the first 10-30 seconds of a stunning process e.g. group wise stunning of pigs. The pre-stunning step makes the animals calm down or sedate and the aversion due to high $CO_2$ concentrations is then reduced or avoided. Aversion reactions may occur when conscious animals are subjected to $CO_2$ concentrations above 30% for larger animal such as pigs and may occur for 10-30 seconds until the animals become unconscious. Poultry may have aversion reactions at much lower $CO_2$ concentrations. With the present invention the animal calm down or sedate slightly due to the presence of $N_2O$ and/or low concentration of $CO_2$ in combination with $O_2$ and the animal will afterwards not show any aversions if final-stunned with high $CO_2$ concentrations, such as $CO_2$ concentration above 30%.

The duration of the pre-stunning process may differ dependent on animal species and may for larger animals such as pigs and ruminants last between 2 sec to 5 min, such as 10 sec to 3 min, e.g. 10-150 sec, such as 10-120 sec, e.g. 30-90 sec, such as 40-80 sec, e.g. 10-90 sec, such as 10-60 sec, e.g. 10-30 sec, such as 20-30 sec, e.g. about 25 sec. Preferably pre-stunning of pigs or ruminants is performed with a pre-stunning gas mentioned herein for about 2-90 sec, e.g. 5-45 sec, such as for 10-30 sec. For finishing pigs the pre-stunning may take about 30 seconds. For poultry the pre-stunning process may last for 2 sec to 30 min as the stunning process generally is longer for poultry than for larger animals.

To avoid aversive reactions among the animals to be stunned the pre-stunning should be performed with the presence of oxygen in the pre-stunning gas, hereby the animals are not subjected to lack of oxygen during the pre-stunning process.

The amount of $N_2O$ in the pre-stunning gas is preferably in the range of lowest possible to be a therapeutic concentration. Preferably the $N_2O$ concentration is 35-75%.

The amount of $CO_2$ in the pre-stunning gas is preferably 5-25% to avoid irritation of the animals but moderately sedative and increases the respiration. Low concentration of $CO_2$ makes the animal breathless and it will increase the breathing hereby drawing $N_2O$ into the body and hereby increasing the effect of $N_2O$.

Examples of combinations of concentrations of different pre-stunning gasses may be:

| Pre-stunning gas combination | $O_2$, % | $CO_2$, % | $N_2O$, % |
|---|---|---|---|
| 1 | 15-21 | 5-10 | 10-15 |
| 2 | 12-17 | 8-12 | 8-12 |
| 3 | 12-17 | 8-12 | 33-37 |
| 4 | 12-17 | 18-22 | 8-12 |
| 5 | 12-17 | 18-22 | 33-37 |
| 6 | 8-12 | 28-32 | 33-37 |
| 7 | 21 | 5 | 10 |
| 8 | 15 | 10 | 10 |
| 9 | 15 | 10 | 35 |

-continued

| Pre-stunning gas combination | O$_2$, % | CO$_2$, % | N$_2$O, % |
|---|---|---|---|
| 10 | 15 | 20 | 10 |
| 11 | 15 | 20 | 35 |
| 12 | 10 | 30 | 35 |
| 13 | 10 | 10 | 45 |
| 14 | 10 | 20 | 45 |
| 15 | 10 | 30 | 50 |
| 16 | 15-21 | 5-10 | 15-40 |
| 17 | 15-21 | 5-10 | 35-50 |
| 18 | 15-21 | 5-10 | 45-75 |
| 19 | 12-17 | 8-12 | 15-40 |
| 20 | 12-17 | 8-12 | 35-50 |
| 21 | 12-17 | 8-12 | 45-75 |
| 22 | 12-17 | 18-22 | 15-40 |
| 23 | 12-17 | 18-22 | 35-50 |
| 24 | 12-17 | 18-22 | 45-75 |
| 25 | 10 | 30 | 60 |
| 26 | 15 | 25 | 55 |
| 27 | 15 | 30 | 50 |
| 28 | 15 | 30 | 45 |
| 29 | 5-15 | 40-60 | 25 |
| 30 | 5-15 | 40-60 | 35 |
| 31 | 5-15 | 40-60 | 45 |
| 32 | 5-15 | 40-60 | 55 |

If the sum of the gas combination in the table does not sum up to 100 the remaining part equals the content of atmospheric air.

Where O$_2$ is mentioned in the list above this may originate as added O$_2$, or from air optionally added O$_2$ and further added CO$_2$ and/or N$_2$O.

Examples of animals which may be pre-stunned with the gas combinations mentioned are mentioned herein below and above.

Another aspect of the invention relates to use of the combination of gas as described herein for pre-stunning of at least one animal.

When pre-stunning of at least one animal with a gas combination as described herein the gas may be dry, humid or in steam such as in water vapour e.g. as aerosols. Preferably the gas combination is made by adding CO$_2$ and/or N$_2$O to atmospheric air optionally further adding O$_2$ if required to reach a pre-determined concentration of oxygen. The non-mixed gases or the gas mixture may be turned into aerosols before use.

The gasses may also be aerified in water, oil or in oil and water, such as in water, plant oil or in plant oil and water. The water, oil and water and oil will bind the gasses to the lung tissue of the animals and at the same time the gasses are also connected to the water and/or oil making it easier to handle the gas in the pre-stunning and/or stunning chamber. The gasses CO$_2$ and N$_2$O are heavier than air. However when making aerosols, the water and/or oil makes the gas-liquid phase even heavier than the gasses alone. Hereby it becomes easier to dose the correct amount of gasses and it becomes easier to evacuate the gasses from the pre-stunning or stunning chamber.

Dry gas is quicker in the inlet and evacuation process than humid gas and gas in steam. Humid gas and gas in steam such as aerosols seem to reduce the risk of gas escape from the pre-stunning system. In systems where the pre-stunning gas is evacuated, this pre-stunning gas may be replaced with atmospheric air or a stunning gas.

Gas in steam such as aerosols may be directed into a pre-stunning and/or stunning chamber in the top part and may be evacuated from the bottom part. Aerosols may be sprayed into the chamber e.g. from a number of nozzles in the ceiling giving a fast distribution of the pre-stunning gas within the chamber.

The gas may be mixed before use i.e. before the at least one animal is exposed to the gas combination for pre-stunning. The gas may also be supplied through one or multiple nozzles into a chamber keeping the at least one animal for pre-stunning. This supply may be with a pre-mixed gas combination or the gasses may mix within the chamber when the different gasses are supplied through different nozzles. When pre-stunning gas is reused this is equivalent to mixing the gasses before use.

As both CO$_2$ and N$_2$O have a relaxing or sedative effect these gasses need not be carefully mixed before exposure to the at least one animal.

In an embodiment the combination of gas is used for pre-stunning of at least one animal which is a livestock.

The livestock may be a mammal, such as ruminants or poultry. The livestock may also be a ruminant such as cattle, sheep, goats. Pigs may be selected from suckling pigs, finishing pigs or sows. Cattle may be selected from cows, dairy cows, calves. Poultry may be selected from hens, chicken, turkeys, ducks, geese. The at least one animal may be selected from the list of pigs, cattle, sheep, goats and chicken, turkeys, ducks, geese.

Preferably the at least one animal is a non-human animal. Most preferably the animal is not a human.

The pre-stunning may be performed for individual animals or group wise for at least two animals.

Use of the combination of gas of any combination described herein for pre-stunning of at least one animal may be performed in any suitable method and systems such as in the method and system as described herein below. For the use the gas concentrations in the pre-stunning gas and duration of the pre-stunning process may be determined due to the type of animal to pre-stun, the number of animals to pre-stun and a final-stunning process.

In an aspect the invention relates to a method for pre-stunning of at least one animal, the method comprises Directing the at least one animal into a system configured for pre-stunning with at least one gas, Introducing the combination of pre-stunning gas as described herein into the system, where the introducing of gas is performed with a mixed or a non-mixed gas combination, Keeping the at least one animal in the system with the pre-stunning of gas for at least 2 seconds, such as at least 5 seconds, Whereby the at least one animal is pre-stunned.

The method is preferably a pre-stunning method based on adding CO$_2$ and/or N$_2$O and/or O$_2$ to atmospheric air or the method is based on a controlled atmosphere comprising at least O$_2$ and CO$_2$ and/or N$_2$O. Preferably the pre-stunning gas comprises O$_2$ (e.g. from atmospheric air used in the pre-stunning gas), CO$_2$ and N$_2$O. The concentrations of these gasses may be as described elsewhere herein.

The method is preferably performed for pre-stunning of livestock.

The gasses may be mixed before the combination enters into a pre-stunning system. The gasses can also be added one at a time through the same nozzles or through different nozzles specific for each gas. The gasses or gas mixture may be in any suitable conditions when being directed into the chamber such as dry or humid e.g. as aerosols.

In an embodiment of the method the pre-stunning is performed with at least two or more animals such that the pre-stunning is performed as a group-wise pre-stunning method. However individual pre-stunning is also possible.

The at least one animal for pre-stunning may be a group of animals such as 2, 3, 4, 5, 6, 7, 8, 9, 10, 11, 12, 13, 14, 15, about 20, about 30, about 40, about 50, about 60, about 70, about 80, about 90, or about 100 animals. Preferably cattle and cows are pre-stunned individually or in groups with less than 10 animals. Preferably pigs, goats and sheep are pre-stunned in groups of 3 to 20 animals such as in groups of 5-10 animals. Preferably chicken or hens are pre-stunned in groups of 15-70 animals. Preferably turkeys or geese are pre-stunned in groups of 10-40 animals.

The at least one animal may be grouped into movable boxes which are positioned in a system for the pre-stunning process and optionally followed by a final-stunning process e.g. prior to a slaughtering process. The boxes for at least one animal may be a box known in the art for e.g. hens, chicken, ducks, turkeys etc.

In another embodiment the method further comprises a final-stunning step performed after pre-stunning of the at least one animal in a gas combination as mentioned herein. The method may further comprise a slaughtering process following the final-stunning process.

The pre-stunning may also be an integrated part of the stunning process as described elsewhere herein.

By including a final-stunning step the method may be a stunning method for stunning of at least one animal where the method has a pre-stunning process and a final-stunning process, the method may comprise the steps of:
  Directing at least one animal into a system configured for pre-stunning with at least one gas, and final-stunning with at least one gas,
  Introducing a pre-stunning gas into the system for pre-stunning of the at least one animal, where the introducing of gas is performed with a mixed or a non-mixed gas combination,
  Keeping the at least one animal in the system with the combination of gas for pre-stunning for at least 2 seconds, such as at least 5 seconds,
  Optionally evacuating $N_2O$ or the pre-stunning gas from the system,
  Directing at least one final-stunning gas into the system for performing final-stunning of the at least one animal,
  Keeping the at least one animal in the system with the final-stunning gas for at least 30 seconds for final-stunning of the at least one animal,
  Whereby said at least one animal is stunned.

In the method described herein the at least one animal may be pre-stunned and final stunned within a single area/box/chamber or the at least one animal may be first pre-stunned in one area/box/chamber and then be moved from this one area/box/chamber to another area/box/chamber where the stunning process is continued eventually leading to final stunning. In a stunning system using gondolas/boxes or a tunnel, the at least one animal are moved from one area to another area during the final stunning process.

The final-stunning gas may be any stunning gas used for stunning of at least one animal. A stunned animal is unconscious. Such final-stunning gasses may comprise at least $CO_2$. For final-stunning the concentration of $CO_2$ is preferably above 70% for pigs and ruminants, and between 5 and 100% for poultry. Poultry are generally kept for a longer period in the stunner making it possible to stun the animals properly with a lower concentration of $CO_2$ than for larger animals such as pigs and ruminants, for whom a faster stunning process requires a higher $CO_2$ concentration of above 60%.

The mentioned amounts of gas may be the amount in atmospheric air added the determined gas or gasses for performing final-stunning of at least one animal e.g. 60% $CO_2$ in atmospheric air.

By pre-stunning following a final-stunning to obtain at least one stunned animal is meant that the stunned animal is unconscious or in a stunned condition or another condition determined by any authority responsible for determining conditions for slaughtering livestock. Such conditions are e.g. described in Regulation (EC) No 1099/2009.

The at least one stunned animal may be slaughtered.

Slaughtering is preferably performed by sticking and/or cutting into the two carotid artery (Latin: arteria carotis externa) of an animal or the blood vessels leading to the carotid arteries and afterwards letting the animal bleed.

The method comprising pre-stunning and final-stunning may also be used for killing at least one animal by keeping the at least one animal in a final-stunning gas until all animals are dead. Preferably killing by the method used herein is performed for sanitary reason e.g. for avoiding transport of infected live animals which should be destroyed to avoid any spread of infections. Such destruction of animals may be performed in a container designed to perform a pre-stunning prior to a final-stunning.

Another aspect of the invention relates to a system for pre-stunning of at least one animal, the system comprising
  At least one pre-stunning chamber comprising an entrance and an exit for entrance and exit of at least one animal, optionally the at least one animal can be enclosed in a gondola or a movable chamber/box,
  At least one gas inlet for directing at least $O_2$, $CO_2$ and $N_2O$ or a combination of the gasses into the pre-stunning chamber,
  At least one gas outlet for evacuating gas from the pre-stunning chamber,
  A control system adapted to control the operation of directing gas into the pre-stunning chamber,
    optionally controlling maintaining a pre-determined concentration of each of the gasses during the pre-stunning step and
    evacuating gas from the pre-stunning chamber.

The gas used for pre-stunning in the system may be any gas combination as described elsewhere herein and in any form as described.

The pre-stunning chamber may be located before a chamber used for a part or for the entire final stunning. The pre-stunning chamber may also be an integrated part of a stunning system such that the pre-stunning chamber is also the chamber for the first part of the stunning process or for the entire stunning process.

The entrance and an exit of the gas tight pre-stunning chamber may comprise an entrance and exit by a transport chamber such as an entrance and exit of a gondola or movable chamber enclosing the at least one animal. It is to be understood that the pre-stunning chamber need only be gas tight at the time it is actually used for pre-stunning and optionally also for final-stunning of at least one animal. When the pre-stunning chamber is an integrated part of a stunning system such as a box within e.g. a gondola system, the pre-stunning chamber is preferably gas tight when used for pre-stunning, but is not gas tight when used for the final stunning where the box or gondola is directed through a volume of stunning gas such as stunning gas in a pit.

The pre-stunning chamber may be a gas tight chamber, a pit and/or a tunnel.

The pre-stunning chamber may be part of a stunning system where the pre-stunning chamber is located before a chamber, pit and/or tunnel for final-stunning. Such chambers, pits and/or tunnels for final-stunning are known.

The system may further comprise at least one sensor or nozzle in the pre-stunning chamber. The at least one sensor or nozzle may be selected from

- At least one sensor for measuring $CO_2$,
- At least one sensor for measuring $N_2O$,
- At least one sensor for measuring $O_2$,
- At least one nozzle for adding $CO_2$,
- At least one nozzle for adding $N_2O$,
- At least one nozzle for adding $O_2$,
- At least one nozzle for adding a re-used pre-stunning gas combination,
- At least one nozzle for evacuating $N_2O$ and/or
- At least one nozzle for evacuating a gas combination comprising at least $O_2$, $CO_2$, and $N_2O$.

In an embodiment the pre-stunning chamber comprises at least one sensor for measuring $O_2$ and/or $CO_2$ and/or $N_2O$ and at least one nozzle for adding gas. Preferably the pre-stunning chamber also comprises at least one nozzle for evacuating gas.

In a preferred embodiment the pre-stunning chamber comprises at least one sensor for measuring CO2, at least one sensor for measuring N2O, at least one sensor for measuring O2, at least one nozzle for adding CO2, at least one nozzle for adding N2O, at least one nozzle for adding O2, at least one nozzle for adding a re-used pre-stunning gas combination, and at least one nozzle for evacuating N2O and/or at least one nozzle for evacuating a gas combination comprising at least O2, CO2, and N2O.

In another embodiment the system further comprises at least one gas storage for storage of pre-stunning gas, such as for re-use of pre-stunning gas within the system.

The system may further comprise at least one gas storage for storage of pre-stunning gas. The at least one gas storage may be for storage of $O_2$, $CO_2$, and $N_2O$ in separate storages. The at least one gas storage may be for storage of at least $O_2$, $CO_2$, and/or $N_2O$ mixed in a ready-to-use combination for pre-stunning of at least one animal. The at least one gas storage may be for storage prior to re-use of a pre-stunning gas comprising at least $O_2$, $CO_2$, and/or $N_2O$. The pre-stunning gas for re-use may be evacuated from the pre-stunning chamber and the gas may comprise evacuated $N_2O$ and/or at least $O_2$, $CO_2$, and $N_2O$ evacuated from the pre-stunning chamber.

The at least one gas storage may be for storage of an amount of pre-stunning gas corresponding to the amount to be used for pre-stunning of at least two times i.e. an amount corresponding to two times the amount to be used for each pre-stunning step, such as for pre-stunning three times, e.g. for pre-stunning four times, such as for pre-stunning five times. However, for small stunning systems the gas storage may be for storage of an amount of pre-stunning gas corresponding substantially to the amount to be used for pre-stunning a single time.

The at least one gas storage for storage of pre-stunning gas to be re-used may be a pit or a closed gas storage. The at least one gas storage may comprise at least one sensor for measuring $CO_2$, at least one sensor for measuring $N_2O$, and/or at least one sensor for measuring $O_2$. The at least one gas storage may further comprise at least one nozzle for adding $CO_2$, at least one nozzle for adding $N_2O$, and/or at least one nozzle for adding $O_2$ and/or atmospheric air making it possible to adjust the concentration of gasses in the gas storage prior to use of the pre-stunning gas.

The system may further comprise transporting means for transporting the at least one animal into a pre-stunning chamber and from a pre-stunning chamber into a final-stunning chamber. The transporting means may be at least one gondola or box for enclosing at least one animal to be pre-stunned and final-stunned prior to slaughter. The at least one gondola or box may transport the at least one animal in an elevator system bringing the animals into a pit for stunning. The transporting means may also be at least one conveyor or conveyor belt for conveying at least one animal enclosed in a box.

In a stunning system for stunning of larger animals such as pigs, lambs, deer, cattle/cows etc. the animal preferably walk by themselves into the pre-stunning chamber. Pre-stunned animals may walk by themselves from a pre-stunning chamber and into a stunning chamber. However, preferably the pre-stunned animals are transported from a pre-stunning chamber to a stunning chamber such as in boxes or at least with a conveying floor supporting the pre-stunned animals.

Preferably the pre-stunning chamber is used for pre-stunning of at least one animal prior to final-stunning and slaughter of the at least one animal. The at least one animal may be any animal mentioned herein.

In an embodiment the system as described herein further comprises gondolas for transporting the at least one animal through a pre-stunning step and a final-stunning step. The gondolas may be air-tight when the pre-stunning step is performed and gas permeable when the final-stunning step is performed. The switch between air-tight and gas permeable may be performed by closing and opening apertures in the gondolas.

Stunning systems with gondolas for transporting the animals are known e.g. from WO 2004/064527 'Method and apparatus for stunning of slaughter animals'.

Reuse of the $N_2O$ or the entire pre-stunning gas combination may be performed e.g. at abattoirs by evacuating at least the $N_2O$ or the entire gas combination from the pre-stunning chamber. If evacuating the entire pre-stunning gas combination from the pre-stunning chamber this gas may be replaced by a gas combination for final-stunning.

The gasses in a pre-stunning gas combination may be added to a pre-stunning chamber e.g. in the top part of the chamber used for the pre-stunning through nozzles.

$N_2O$ or the entire pre-stunning gas combination may be evacuated from the pre-stunning chamber e.g. from the lower part of the pre-stunning chamber. This pre-stunning gas may be stored in a gas storage as described elsewhere. The evacuated pre-stunning gas may be reused in subsequent pre-stunning processes for pre-stunning of other animals. From the evacuated pre-stunning gas one or more gasses may also be separated from the mixture e.g. $CO_2$ may be separated from the gas mixture by freezing.

The gasses or gas combination (=gas mixture) may be directed into the chamber used for pre-stunning of animals such as into a pre-stunning chamber in the form of aerosols e.g. by directing the gas such as aerosols into the chamber preferably through in-lets/nozzles in the ceiling and/or in the top part of at least one wall of the chamber. The gas may be evacuated through outlets/nozzles at least in the ceiling, one wall and/or the floor of the chamber. For aerosols the inlet may be through the ceiling and the evacuating may be through the floor and/or bottom part of at least one of the walls, such as through 'skirts' in the walls i.e. longitudinal openings along the bottom part of the walls.

Figure 2:
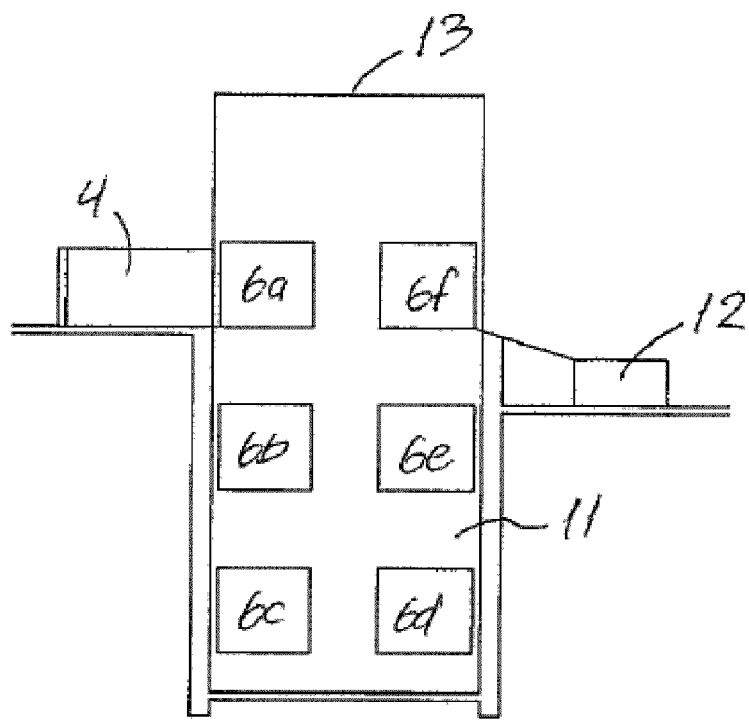
FIG. 2 illustrates a stunning system for pigs with the entrance, exit and underground pit for final-stunning gas.

The system as described herein may be a stunning system for stunning of pigs and which is based on e.g. 5-7 gondolas which each may enclose a group of e.g. 7 or 8 pigs during the pre-stunning and final-stunning processes and where the pigs in a gondola when being final-stunned may be directed down ward into a pit comprising at least 70% $CO_2$ and upward again when nearly final stunned. Smaller or larger systems is also suitable such a systems with less than 5 gondolas or more than 7 gondolas or systems with gondolas for fewer or more pigs. FIG. 2 illustrates a stunning system with 6 gondolas, where the gondolas has 6 positions in the stunning system (6a, 6b, 6c, 6d, 6e, and 6f) before a gondola returns to a start position (6a) for another tournament. In a tournament of e.g. about 3 minutes from the start position through stunning and back to the start position each gondola may be about 30 seconds in each position. The start position (6a) is for entering the at least one animal into the gondola and the end position (6f) of the gondola is for exit of the at least one animal when these are stunned. In such a system at least the first position (6a) and/or the second position (6b) may be used for pre-stunning of the at least one animal. The two first positions of the gondola system may be used for pre-stunning e.g. by adding a pre-stunning gas in the first position (6a) and evacuating at least part of the pre-stunning gas in the second position (6b) or while the gondola is conveyed from the first position (6a) to the second position (6b).

Each gondola may comprise a pre-stunning chamber which may be designed such that each gondola may be controlled to be air-tight when used for pre-stunning. In this way a pre-stunning chamber need not be a chamber separate from a chamber used for stunning such as for final stunning of at least one animal.

In positions for pre-stunning (position 6a and/or 6b) the gondolas are preferably air-tight and in the following positions (6c to 6e and optionally 6f) the gondolas are preferably gas permeable. Apertures may be opened and closed to make the gondola gas permeable and air-tight, respectively. A safety system may secure apertures are closed if $N_2O$ of at least a pre-determined level is measured within a gondola. Hereby a gondola in position 6a and/or 6b may be equivalent to a pre-stunning chamber.

A stunning process based on the gondola-system may comprise pre-stunning in at least one position while the gondolas move or in a pre-position before the final-stunning process begin. Also the first two positions of the gondola system may be for pre-stunning according to the method described herein. The pre-stunning process when stunning of e.g. pigs may last between 10 sec to 3 min, e.g. 10-150 sec, such as 10-120 sec, e.g. 10-90 sec, such as 10-60 sec, e.g. 10-30 sec, such as 20-30 sec, e.g. about 25 sec.

A stunning system based on a gondola system for pre-stunning and final-stunning of at least one animal such as group-wise stunning of pigs may comprise e.g. 5, 6 or 7 gondolas and the pre-stunning gas may be re-used. The re-use of pre-stunning gas may be performed in a way such that at least one storage for pre-stunning gas is located in the stunning system e.g. within a center position of the gondola system. The at least one storage (9) for pre-stunning gas may be used for storage of pre-stunning gas which are used when directing at least part of it into a gondola in a start position (6a) or shortly after the gondola has left the start position or has reached the second position (6b). Pre-stunning gas evacuated from a gondola may be directed to at least one storage (10) or be returned to the storage (9) from where it entered into the gondola. A gondola system for pre-stunning and stunning of animals may be used for any animal mentioned herein.

Instead of a gondola system the system may be based on boxes or chambers which are conveyed through areas with pre-stunning and/or stunning gasses such as in tunnel(s) and/or in pits. Such a system may be used for any animal mentioned herein.

The pre-stunning chamber may also be a separate chamber i.e. separate from the chamber for final-stunning, and in the pre-stunning chamber it may be possible to quickly establish and evacuate a controlled atmosphere consisting of: a low $CO_2$-concentration, preferably between 5-30%, normal concentration of $O_2$, and varying concentrations of $N_2O$. Preferably it should be possible to infuse gasses and evacuate the gas blend before releasing the pre-stunned pigs, in order to recycle the $N_2O$-containing gas mixture. The released pre-stunned pigs preferably proceed into a stunning chamber to become stunned.

The pre-stunning chamber may be an integrated part of a $CO_2$ stunning facility, either integrated in the actual $CO_2$-stunner, or integrated between the stunner and the driveway.

The pre-stunning is expected to render the animals such as pigs conscious, unconscious, or just sedated. The pre-stunning facility should preferably be able to handle both conscious and unconscious animals, and preferably the animals should therefore not be moved into a new compartment/box before the final-stunning such as actual $CO_2$-stunning. The at least on animal such as pigs which are to be stunned may be driven onto a gondola or similar, where they remain until they are tipped out after stunning (including pre-stunning and final-stunning). The flow for stunning of at least one animal, such as pigs may be:

1: Driving, as it is done today, group wise or otherwise.
2: The sliding wall that normally drives the group of pigs into the stunner may be similar to the existing one, and drive the pigs into a compartment similar to the existing gondolas or a similar box, where the pigs are kept until stunning is completed.
3: The gondola/box is inserted into a pre-stunning compartment, an airtight compartment is closed, pre-stunning gas is infused, keeping for a pre-stunning period, gas is evacuated, the compartment is opened into the stunner, and the gondola/box containing the pre-stunned animals such as pigs moves on into the $CO_2$-stunning facility for final-stunning.

This pre-stunning could either take place in a pit type of stunner or be a separate part of a stunning tunnel. The pre-stunning unit could be added to existing facilities or integrated in new facilities.

For poultry pre-stunning may be performed as the initial phase of a stunning tunnel. The tunnel may comprise separation devices capable of separating the tunnel into different zones. The separation devices may be capable of isolating a pre-stunning gas from the stunning gas. The separation devices in a stunning tunnel may be curtains, such as lamella curtains ensuring minimal leakage of gas between the zones. The separation devices may also be doors such as automatic doors, securing a gas tight zone. Directing pre-stunning gas and evacuation of pre-stunning gas may be performed as described elsewhere herein. Poultry pre-stunned in a tunnel may also be final stunned in the same tunnel. Poultry may also be pre-stunned in the tunnel to become relaxed and pain-relieved, suspended and electrical stunned.

DETAILED DESCRIPTION OF THE FIGURES

FIG. 1 illustrates a stunning system for pigs seen from above. Pigs (3) are led along a driveway (1) by a push hoist gate (2) to an entrance area (4) and pushed by a sliding wall (5) into a stunning box or gondola in its start position (6a) where pre-stunning gas is led into the box through nozzles (indicated by arrows 7) and evacuated from the box (indicated by arrows 8). Pre-stunning gas is stored in a storage (9) before it is directed into the box or gondola (6a) including the pigs to be stunned. Preferably pre-stunning gas is led into a box or gondola when the box or gondola (6a) is in the start position and/or while it is conveyed to a second position in the stunning system. The pre-stunning gas is evacuated from the box or gondola and into a storage (10) which may be in contact with the storage (9) making it possible to re-use the pre-stunning gas. The box or gondola (6) is directed into a pit (11) with final-stunning gas and to the end position (6f) i.e. an emptying area where stunned pigs are let out of the box or gondola (6f) to a conveyor belt (12) transporting the pigs to a slaughtering site.

FIG. 2 illustrates a side view of the stunning system for pigs as also illustrated in FIG. 1. Pigs (not shown) is led along a drive way (1) to an entrance area (4) and into a box or gondola in a start position (6a) where it can be pre-stunned as indicated in FIG. 1. The box or gondola (6) is conveyed into a pit (11) with gas for final-stunning where the pre-stunned animals are stunned in the conveying of the box or gondola along the positions in the pit (6b, 6c, 6d and 6e). The pigs are stunned before the box or gondola is conveyed to the end position (6f) where the pigs are directed towards a conveyor belt (12) transporting the pigs to a slaughtering site. A ceiling or house (13) above the pit (11) and enclosing all of the gondolas (6a-6f) in the stunning system is also illustrated. The floor level is just beneath the drive way (1) and entrance area (4) on one side of the pit and just beneath the conveyor belt (12) on the other side of the pit.

Figure 3:
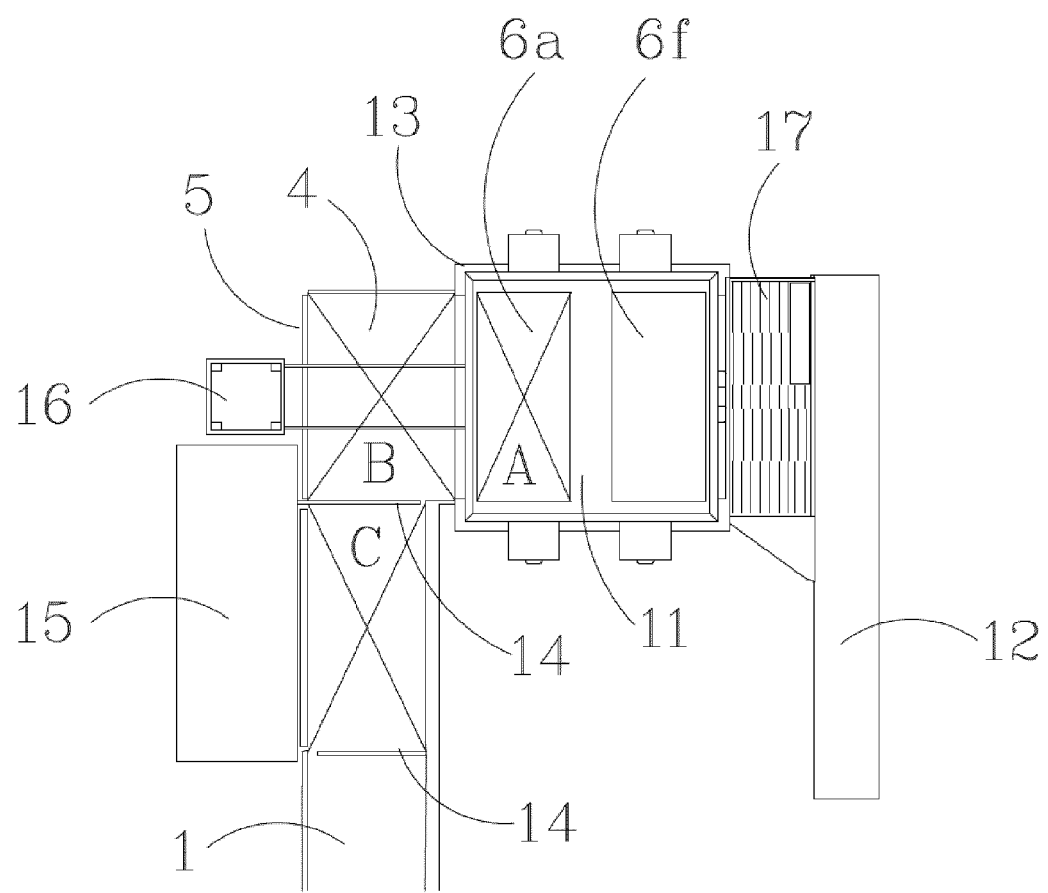
FIG. 3 illustrates the stunning system of FIG. 1 where possible areas for pre-stunning are indicated.

FIG. 3 illustrates the stunning system of FIG. 1 where some possible areas for pre-stunning are indicated. Pre-stunning may be performed before the animals enter into a stunning system or in the first part of the stunning system. In this figure some possible pre-stunning areas are indicated in connection with a stunning system including gondolas bringing the animals into a pit with stunning gas, however the principle of locating the pre-stunning before or as an integrated part of a stunning system may also be performed with other stunning systems. Pre-stunning may be performed in the gondolas (6a) indicated by A, in the entrance area (4) indicated by B and/or in the drive way (1) indicated by C. A stunning system may be designed with the pre-stunning area A, B or C i.e. only pre-stunning area, or a stunning system may be designed with two or three pre-stunning areas such as pre-stunning areas A+B, A+C, B+C or A+B+C. The situation with a stunning system with the pre-stunning area A is described elsewhere herein. A pre-stunning system with the pre-stunning areas A+B may have a pre-stunning box located at area B i.e. in the entrance area (4) of the stunner such a pre-stunning box is preferably capable of being air-tight when in function for pre-stunning animals. When the animals are pre-stunned in pre-stunning area B and/or C they are preferably capable of walking by themselves into the stunning gondola (6a), or they may be conveyed into the stunning gondola (6a). Conveying of animals may be performed by a moving/conveying floor or the animals may be inside a box which is conveyed. A pre-stunning box may have any suitable dimensions such as about 2.5*1.8 m in ground level and about 1 m high when used for stunning of a group of 7-8 pigs.

LIST OF ITEMS ILLUSTRATED IN THE FIGURES

1. Drive way
2. Push hoist gate
3. Pigs
4. Entrance area
5. Sliding wall
6. a-f: box/gondola for pre-stunning and final-stunning where a-f illustrate different gondola positions within the stunning system.
7. Inlet for pre-stunning gas
8. Outlet for pre-stunning gas for evacuation of pre-stunning gas
9. Storage for pre-stunning gas
10. Storage for evacuated pre-stunning gas
11. Pit for final-stunning comprising final-stunning gas (final-stunning gas is not shown)
12. Conveyor belt
13. Ceiling (house) above pit
14. Gate
15. Guideway for gate
16. Frame for sliding wall
17. Exit area e.g. with rollers
A. Possible pre-stunning area: Within the stunning area
B. Possible pre-stunning area: In the entrance area
C. Possible pre-stunning area: In the last part of the drive way Example During ongoing work with $CO_2$-stunning of pigs where the stunning process was surveyed by video cameras it was observed that finishing pigs became unconscious by an unintended prolonged presence of $CO_2$ concentrations as low as 17-20%. In these cases no panic occurred among the pigs, only the normal physiologic reaction to elevated blood $CO_2$ was observed, which is gasping (increased respiration depth and frequency). The prolonged presence of a low $CO_2$ concentrations corresponded to simultaneously prolonged presence of higher $O_2$ concentrations than normal during the initial phase of the stunning process.

Based on the observation of prolonged presence of low $CO_2$ concentration and higher $O_2$ concentrations in the initial phase of the stunning process the presence of sufficient $O_2$ during a pre-stunning process is thought to be important because the physiologic effect of asphyxia is unwanted during pre-stunning.

The invention claimed is:

1. A combination of gas for pre-stunning and final stunning of at least one animal, said combination of gas comprising:
   at least air; and
   O2, together with N2O and CO2.

2. The combination of gas according to claim 1, wherein a concentration of the O2 is between 5 and 26%; a concentration of the CO2 is between 5 and 60%, and a concentration of the N2O is between 5 and 75%.

3. The combination of gas according to claim 2, wherein the concentration of CO2 is below 40%.

4. The combination of gas of claim 1, configured for use for pre-stunning of at least one animal.

5. The combination of gas according to claim 4, wherein the at least one animal is a livestock.

6. A method for pre-stunning of at least one animal, said method comprising:
   directing said at least one animal into a system configured for pre-stunning with at least one gas;
   introducing a combination of gas comprising at least air and O2, together with N2O and CO2 into said system, where said introducing of said combination of gas is performed with a mixed or a non-mixed gas combination; and
   keeping said at least one animal in said system with said combination of gas for at least 5 seconds;

whereby said at least one animal is pre-stunned.

7. The method according to claim 6, wherein said at least one animal is two or more animals.

8. The method according to claim 7, wherein the pre-stunning is performed as a group-wise pre-stunning method.

9. The method of claim 6, further comprising a final-stunning step performed after keeping said at least one animal in said combination of gas for at least 5 seconds.

10. The method according to claim 6, wherein a concentration of $CO_2$ is below 40%.

11. A system for pre-stunning and final stunning of at least one animal, said system comprising:
   at least one pre-stunning chamber comprising an entrance and an exit for entrance and exit of at least one animal;
   at least one gas inlet for directing at least $O_2$, $CO_2$ and $N_2O$ or a combination of said gasses into said pre-stunning chamber;
   at least one gas outlet for evacuating gas from said pre-stunning chamber;
   a control system adapted to control the operation of:
      directing said at least one gas into said pre-stunning chamber;
      maintaining a pre-determined concentration of each of said gasses during a pre-stunning step; and
      evacuating said at least one gas from said pre-stunning chamber.

12. The system according to claim 11, further comprising at least one gas storage for storage of pre-stunning gas.

13. The system according to claim 12, wherein said at least one gas storage fir storage of pre-stunning gas is configured for re-use of pre-stunning gas within the system.

14. The system according to claim 11, further comprising gondolas for transporting the at least one animal through a pre-stunning step and a final-stunning step.

15. The system according to claim 11 wherein the least one pre-stunning chamber further comprising a gondola or a movable chamber configured to enclose said at least one animal.

* * * * *